United States Patent [19]
Von Hoff et al.

[11] Patent Number: 4,772,261
[45] Date of Patent: Sep. 20, 1988

[54] INTRAMEDULLARY CATHETER

[75] Inventors: Daniel D. Von Hoff; John G. Kuhn, both of San Antonio, Tex.; Paul W. Leighton; Howard M. Wakeman, both of Thiensdille, Wis.

[73] Assignee: Board of Regents, The University of Texas System, Austin, Tex.

[21] Appl. No.: 8,874

[22] Filed: Jan. 29, 1987

[51] Int. Cl.⁴ ............................................. A61M 25/00
[52] U.S. Cl. ..................... 604/51; 604/175; 604/264
[58] Field of Search ............... 604/51, 93, 175, 264, 604/272–274; 128/754

[56] References Cited

U.S. PATENT DOCUMENTS

| | | | |
|---|---|---|---|
| 2,426,535 | 8/1947 | Turkel | 128/754 |
| 3,298,372 | 1/1967 | Feinberg | 604/8 |
| 3,310,051 | 3/1967 | Schulte | 604/175 |
| 3,752,162 | 8/1973 | Newash | 604/93 |
| 3,853,127 | 12/1974 | Spademan | 604/167 |
| 4,177,814 | 12/1979 | Knepshield | 604/167 |
| 4,261,357 | 4/1981 | Kontos | 604/167 |
| 4,400,169 | 8/1983 | Stephen | 604/49 |
| 4,413,985 | 11/1983 | Wellner et al. | 604/264 X |
| 4,490,137 | 12/1984 | Moukheibir | 604/28 |
| 4,491,126 | 1/1985 | Cullor | 128/1 R |
| 4,494,535 | 1/1985 | Haig | 128/92 YK |

OTHER PUBLICATIONS

Turkel et al.,-War Medicine, Apr. 1944, vol. 5, pp. 222-225.

Primary Examiner—Dalton L. Truluck
Attorney, Agent, or Firm—Arnold, White & Durkee

[57] ABSTRACT

An intramedullary catheter is provided which is attached to a bone to permit the infusion of drugs, fluids, or the like, directly into the bone marrow for subsequent dispersion to the vascular system. The present invention contemplates an intramedullary catheter, method of implanting such a catheter, and a method of fluid delivery to the vascular system through the bone marrow. The intramedullary catheter preferably includes a threaded conduit, a head attached to one end of the conduit, and a sealing membrane in the head overlying the conduit. The intramedullary catheter is implanted in a bone, such as the iliac crest, with the conduit threadingly engaging the bone and the surrounding skin closed over the head and membrane. Fluids are delivered by inserting a needle through the membrane into communication with the conduit for transport to the bone marrow. The present invention is particularly appropriate for patients who require long-term administration of medications as an alternative to intravenous delivery.

14 Claims, 1 Drawing Sheet

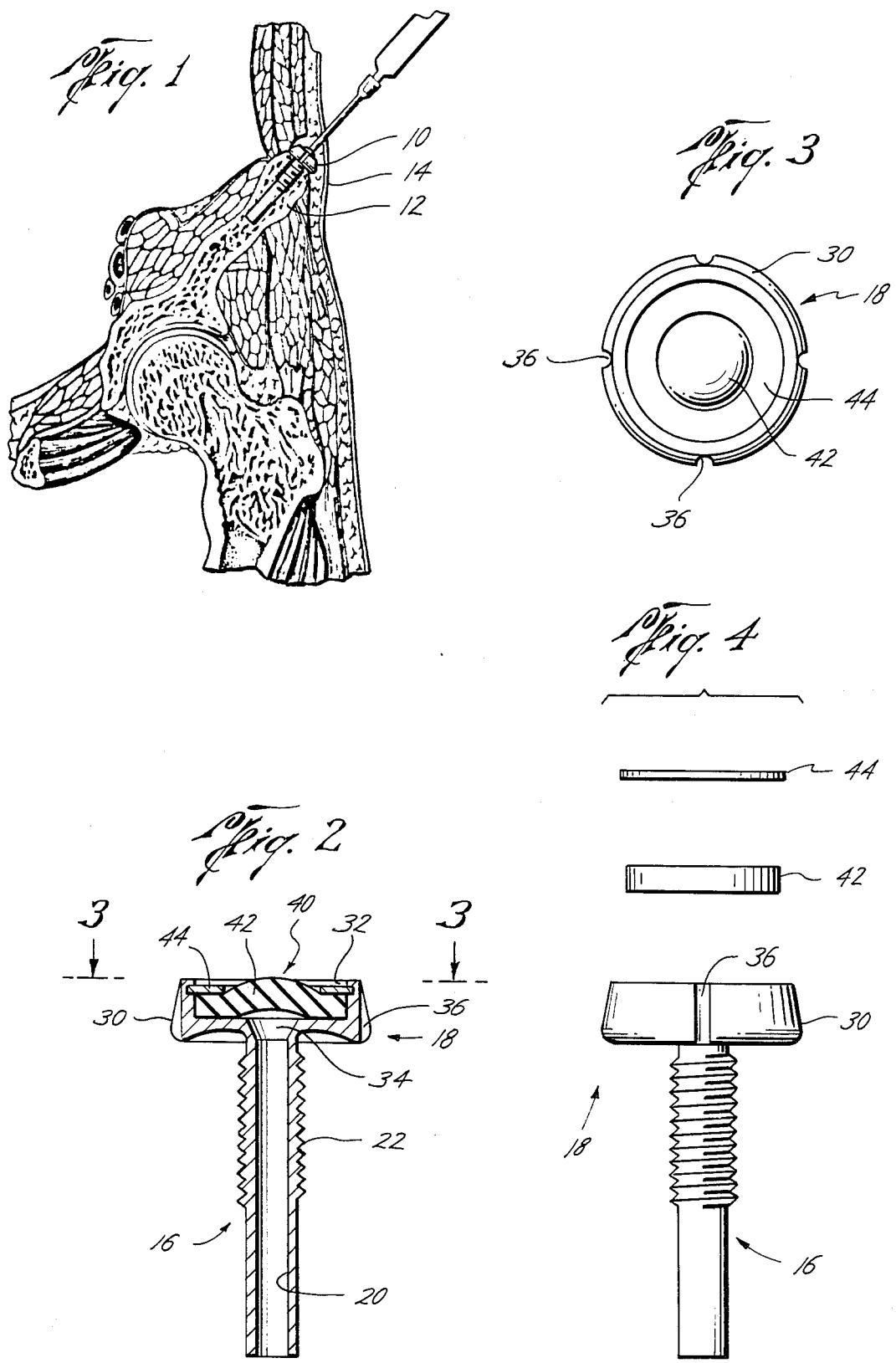

INTRAMEDULLARY CATHETER

BACKGROUND OF THE INVENTION

1. Field of the Invention

This invention relates to a device for delivering fluids to the vascular system through the bone marrow cavity, a method of implanting such a device, and a method of using such a device. In particular, the device comprises an intramedullary catheter which is implanted in a bone and covered by the skin, providing access for the administration of fluids through the bone marrow into the vascular system.

2. Description of the Relevant Art

Intravenous devices are commonly used for the delivery of fluids, such as drugs or the like, directly to the vascular system. Most hospital patients are fitted with an intravenous device to provide the physician with easy access to the vascular system for the administration of such fluids. The advantages of intravenous devices for quickly delivering medication to the vascular system are readily apparent, there are, however, a number of disadvantages.

In using intravenous devices, for example, infection of the surrounding tissue (celulitis) and systemic infection (bacteremia) can sometimes occur. Further, clotting of the vein (thrombosis) and accidental injection of the medication outside of the vein—causing extensive tissue destruction—also occur with some regularity. Perhaps the greatest problem with such intravenous devices is simply the procedure involved in inserting such devices. Often, locating the vein in which such an intravenous device can be placed is difficult, subjecting the patient to a painful ordeal as the doctor or nurse probes the area under the skin in an attempt to find a vein. All of these problems are particularly magnified in those patients requiring long-term (e.g. greater than two weeks) administration of medication.

As an answer to the well known deficiencies of conventional intravenous devices, several systems have been developed for use as an alternative. One such device is the Hichman Broviac silastic catheter which is tunneled under the skin, usually in the chest, and inserted into a large vein, usually the subclavian vein. Other such systems include the Port-a-cath Infus-a-port (sold by Infasaid), and the Mediport (sold by Norfolk) which are essentially cavity structures which are implanted under the skin and have a self-sealing septum. Medication is injected through a needle inserted through the skin and septum into the cavity. A catheter leads from the cavity to the vein to deliver the medication to the vein.

While such implant devices are sometimes a desirable alternative to an intravenous device, a number of problems still exist. For example, infection and clotting in the vein and catheter are still major problems. Further, these implant devices require minor surgery for insertion, and are nevertheless difficult to implant in children. Further, the bulge caused by such implant devices are cosmetically unappealing.

Perhaps the greatest difficulty with such implant devices is that because of the many complications that can arise, many such implant devices must be prematurely removed from the patient. Thus, while such implant devices are often a desirable alternative to intravenous devices, in practice many problems exist with such implant devices.

SUMMARY OF THE INVENTION

The problems outlined above are in large measured solved by the method and device of the present invention. That is, the intramedullary catheter hereof provides convenient access to the vascular system without the major infection, clotting, cosmetic, and insertion problems associated with intravenous devices and such implant devices. The intramedullary catheter of the present invention is particularly appropriate where the patient requires long-term administration of medication.

Broadly speaking, the present invention contemplates a device, alternatively known as an intramedullary catheter or osteoport, which is attached to a bone for providing access for fluid delivery to the vascular system. The device includes a tubular conduit which is inserted through a bore in the bone in communication with the bone marrow cavity. A head is attached to one end of the conduit to lay adjacent the bone such that the surrounding skin can be closed about the head. The head includes a seal mechanism which overlies the conduit and permits the insertion of a needle through the seal mechanism to deliver the fluid or other medication to the conduit for transport to the bone marrow. It has been found that many medications delivered to the bone marrow are rapidly dispersed throughout the vascular system.

The present invention also contemplates a method of fluid or drug delivery to the vascular system of a patient which includes such an intramedullary catheter. In the method of fluid delivery, the intramedullary catheter is implanted in a bone with the conduit in communication with the bone marrow cavity by drilling a bore into the bone and inserting the conduit into the bore. Preferably, the bore in the bone is tapped with threads and the conduit has threads along a portion such that the catheter is screwed (threadingly secured) into the bore. The drug or other fluid is injected through the overlying skin into the conduit for delivery to the bone marrow and transport to the vascular system. The present invention additionally contemplates a method of implanting a drug delivery device such as the intramedullary catheter of the present invention.

BRIEF DESCRIPTION OF THE DRAWINGS

FIG. 1 represents a fragmentary anatomical sectional view of the iliac crest with the intramedullary catheter of the present invention implanted therein;

FIG. 2 is a sectional view of the intramedullary catheter of the present invention;

FIG. 3 is a top plan view of the head of the intramedullary catheter taken along line 3—3 of FIG. 2; and FIG. 4 is an elevational view of the intramedullary catheter of the present invention with the sealing mechanism exploded for clarity.

DESCRIPTION OF THE PREFERRED EMBODIMENT

Turning now to the drawing, FIG. 1 illustrates an intramedullary catheter 10 implanted in a bone 12 such as the anterior iliac crest, with the skin and surrounding tissue 14 overlying the catheter 10. As shown in FIGS. 2–4, the intramedullary catheter 10 broadly includes an elongated tubular conduit portion 16 and a head portion 18.

As can be seen readily from FIG. 2, the conduit 16 is elongated and needle-like to define a passage 20. The outer portion of the conduit 16 includes a mechanism for attaching the conduit 16 to bone 12, which in the preferred embodiment comprises the threads 22. The distal end of the conduit 16 (remote from the head 18) is simply a flat surface, but in alternative embodiments may comprise the sharpened point.

The head 18 comprises an enlarged circular saucer 30 concentrically attached to the conduit 16 and preferably defining a cylindrical cavity 32. Structure defining a truncated cone-shaped bore 34 connects the cavity 32 with the passage 20. The outer periphery of the saucer 30 includes a plurality of circumferentially spaced apart notches 36 (see FIGS. 3 and 4).

A seal mechanism 40 is interfitted into the cavity 32 as shown in FIG. 2. The seal mechanism includes a silastic self-sealing membrane 42 which is complementally dimensioned for sliding reception into the cavity 32. As can be appreciated from FIG. 2, the membrane 42 is slightly enlarged relative to the cavity 32 so that the perimeter of the membrane 42 sealingly engages the internal walls of the saucer 30 defining the cavity 32, causing the central portion of the membrane 42 to outwardly bulge as shown in FIG. 2. An annular retaining washer 44 is interfitted in an annular groove in the saucer walls defining the cavity 32. The washer 44 overlys the membrane 42, retaining the membrane 42 in position in the cavity 32.

The catheter 10 can be implanted in many different bones in the skeletal structure with the iliac crest 12 shown in FIG. 1 a preferred entry location. In the method of implanting the catheter 10, a small incision in the skin 14 is made in the region of the iliac crest 12 and the iliac crest 12 positively identified through the incision. After identification of the iliac crest, a bore is drilled through the bone 12 into communication with the marrow cavity as shown in FIG. 1. An internal thread is tapped into the iliac crest 12 utilizing a thread size and tap used routinely in orthopedic practice for inserting pins in bones.

The catheter is inserted through the incision in the skin 14, with the distal end of the conduit 16 disposed in the threaded bore in the iliac crest 12. The catheter 10 is then screwed into the iliac crest 12 such that the catheter 10 is secured in the bone 12 by the threads 22. In the preferred method of implantation, a driving tool (not shown) is fitted to the catheter 10 and includes four spaced apart lugs which interfit into the notches 36, such that rotation of the driving tool screws the catheter 10 into the bone 12.

As can be seen in FIG. 1, with the catheter 10 fully inserted in the bone 12, the head 18 abuts the external surface of the bone 12 and the skin 14 is closed over the head 18.

The use of the catheter 10 contemplates a fluid delivery method to the vascular system through the bone marrow cavity. As used in the present application, the term "fluids" is used broadly to include drugs and other medications. To deliver the fluids to the catheter 10, the region of the skin 14 surrounding the catheter 10 is prepped and the needle on the end of a conventional intravenous tubing is inserted through the skin 14 and into the membrane 42. Preferably, the distal tip of the needle is inserted through the membrane 14 and positioned somewhere in the region of the passage 20 proximate the bore 34. Typically, the needle includes a threaded or luer-type hub that can be connected to a variety of external delivery systems. Normally, the needle is connected by tubing to an infusion bottle.

In use, the drugs or other fluids are administered through the catheter 10 into the bone marrow cavity. It has been found that where drugs are injected into bone marrow cavity, that the drugs are rapidly absorbed from the marrow cavity. In many instances, the drugs are delivered as rapidly to the vascular system through the marrow cavity as in direct infusion into a vein.

In practice, it is believed that the catheter 10 and methods of implantation and use offer many advantages over conventional drug delivery procedures. For example, there are no clotting problems in that the catheter 10 is not located in a vein, and similarly, the probability of infection is dimensioned. Once the catheter 10 is inserted, there are no cosmetic disfigurations and little or no chance for occlusion or migration of the catheter 10. The cost of inserting the catheter 10 is minimal, and it can be easily inserted in historically more difficult patients such as infants and geriatrics or other long term care patients. Finally, there is no chance for pneumothorax and no chance for leakage of toxic drugs outside of the desired location, as is possible with intravenous devices.

In summary, it is believed that the catheter 10 and methods of implantation and drug delivery offer a notable advance over the art. In particular, the catheter and methods of the present invention represent a significant advance for patients requiring long term administration of fluids.

We claim:

1. A method of repetitive fluid delivery into the vascular system of a patient, comprising the steps of:
   providing a device having an elongated, tubular conduit, and a head attached to one end of the conduit;
   implanting the device into a bone with the conduit in operable communication with the bone marrow and the device connected to the bone for repetitive use, including the substeps of
   drilling a bore into the bone,
   inserting the conduit into the bore,
   closing the skin adjacent the device to overlay the head;
   injecting a fluid through said overlying skin into the conduit for delivery through the conduit into the bone marrow and transport to the vascular system; and
   repeating the injecting step for repetitive, relatively long term delivery of fluid to the patient.

2. The method according to claim 1, including the steps of:
   providing the device with a sealing mechanism disposed in the cavity to overly the conduit; and
   injecting the fluid through the sealing mechanism into the conduit.

3. The method according to claim 1, including the steps of:
   providing the device with threads along a portion of the external surface of the conduit; and
   the implanting step including the substeps of
   tapping a set of threads in the bone, and
   screwing the conduit into the bore to connect the device to the bone.

4. The method according to claim 1, wherein the device is implanted in the iliac crest.

5. A device attachable to a bone for providing access for fluid delivery to the vascular system, the device comprising:
   an elongated, tubular conduit insertable in a bore in the bone and having a distal end with means for communicating with the bone marrow with the conduit inserted in said bone;

means coupled to the conduit for attaching the conduit to the bone with the conduit inserted in the bore and the communicating means disposed in said bone marrow; and a head attached to the proximal end of the conduit such that with the distal end of the conduit inserted in the bore with said communicating means disposed in said bone marrow, at least a portion of the head is disposed outside the bone, the head including seal means overlying the conduit for permitting repetitive insertion of a needle through the seal means to deliver fluid to the conduit for transport to the bone marrow and subsequent dispersion to the vascular system, and to seal the conduit after withdrawal of the needle to prevent infection from entering the bone marrow.

6. The device according to claim 5, wherein the attaching means comprises a plurality of threads along a portion of the exterior surface of the conduit.

7. The device according to claim 5, wherein the head comprises an enlarged circular saucer defining a cavity therein.

8. The device according to claim 7, wherein the seal means comprises a silastic self-sealing membrane disposed within the cavity of the head.

9. The device according to claim 8, wherein the head includes a washer adjoining the membrane for retaining the membrane in the cavity.

10. The device according to claim 5, wherein the head comprises a circular saucer concentrically oriented relative to the conduit and oriented generally perpendicular to the longitudinal axis of the conduit.

11. The device according to claim 5, wherein the head includes a plurality of spaced apart notches adapted for engaging a tool for screwing the device.

12. A method of implanting a drug-delivery structure in a bone comprising the steps of:

incising the skin overlying the bone;

drilling an elongated bore into the bone in communication with the bone marrow cavity;

tapping a thread in a portion of the bore;

screwing an elongated, threaded, tubular conduit having distal and proximal ends into the bore, with the proximal end disposed adjacent the bone for receiving drugs and the distal end in communication with the bone marrow for delivering drugs to the bone marrow; and closing the skin over the conduit.

13. The method according to claim 12, wherein the proximal end of the elongated, threaded conduit is attached to a head, and screwing the conduit and head into the bore until the head abuts the bone.

14. The method according to claim 13, the closing step including closing the skin over the head.

* * * * *